United States Patent [19]

Langbein et al.

[11] Patent Number: 5,767,279

[45] Date of Patent: Jun. 16, 1998

[54] ENANTIOMERICALLY PURE PYRIDYLCYCLOALKYLETHYLAMINES AND THE SALTS THEREOF AND PROCESSES FOR PREPARING THEM

[75] Inventors: Adolf Langbein, Gau-Algesheim; Heinrich Schneider, Ingelheim am Rhein; Gerd-Rainer Bressler, Bingen am Rhein, all of Germany

[73] Assignee: Boehringer Ingelheim GmbH, Ingelheim, Germany

[21] Appl. No.: 513,582

[22] Filed: Aug. 10, 1995

[30] Foreign Application Priority Data

Aug. 12, 1994 [DE] Germany ............... 44 28 531.0

[51] Int. Cl.[6] .............................. C07D 213/38
[52] U.S. Cl. .............................. 546/329
[58] Field of Search ........................ 546/329

[56] References Cited

FOREIGN PATENT DOCUMENTS 0535521   4/1993   European Pat. Off. .

OTHER PUBLICATIONS

Falorni et al., "Chiral Ligands Containing Heteroatoms; 9. General Procedures For the Synthesis of Optically Active 1-(2-Pyridyl)alkylamines from α-Amino Acids", *Synthesis*, pp. 972–976 (1972).

Lazer et al., "Benzoxazolamines and Benzothiazolamines: Potent, Enantioselective Inhibitors of Leukotriene Biosynthesis with a Novel Mechanism of Action", *J. Chem. Ed.* 37, pp. 913–923 (1994).

Miao et al., "A Simple and Effective Enantiomeric Synthesis of a Chiral Primary Amine", *Tetrahedron Letters*, 34, pp. 2259–2262 (1993).

Miao et al., "The Resolution of Racemic Amides by the Formation of Diasteromeric Amides with Amino Acids", *OPPI Briefs*, pp. 87–91 (1992).

Mi et al., *Chemical Abstracts*, vol. 119, No. 7, Abstract No. 72857h (1993).

*Primary Examiner*—Amelia Owens
*Attorney, Agent, or Firm*—R. P. Raymond; Wendy Rieder; Alan R. Stempel

[57] ABSTRACT

The present invention relates to new enantiomerically pure pyridylcycloalkylethylamines of formula 1a and 1b, the salts thereof as well as to methods of preparing them and their use as intermediate products.

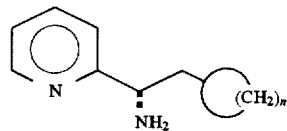

1a

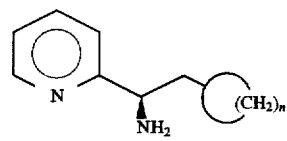

1b

3 Claims, No Drawings

ENANTIOMERICALLY PURE PYRIDYLCYCLOALKYLETHYLAMINES AND THE SALTS THEREOF AND PROCESSES FOR PREPARING THEM

The present invention relates to new enantiomerically pure pyridylcycloalkylethylamines of general formulae Ia and Ib, wherein n denotes an integer 2, 3, 4, 5, 6 or 7, the salts thereof and processes for preparing them.

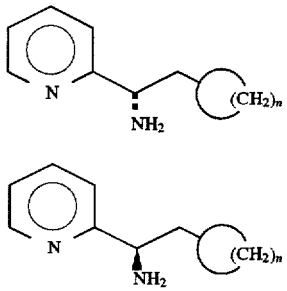

Such amines are important educts for the synthesis of condensed oxazole and thiazole derivatives which are leukotriene-biosynthesis inhibitors and, by virtue of this property, can be used as effective drugs in the treatment of asthma, inter alia. Compounds of this type are already known from the prior art [European Patent Application No. 0 535 521].

Processes for preparing such amines are also known from the art. Thus, one possibility is to obtain the 2-pyridyl-1,3-oxazolidine derivative, correspondingly substituted in the 4-position, which is in equilibrium with its imine, by reacting 2-pyridine-carboxaldehyde with a suitable amino alcohol (cf. the following scheme). By further reaction with a cyclohexylmethylmagnesium halide in the course of a Grignard addition the corresponding diastereomeric cycloalkylpyridylmethylamines can be prepared which, after oxidative cleavage of the derivatised hydroxyethyl substituent, yield the desired chiral amine. The ratio of the two diastereomeric amines is 87:13, when the substituent Y denotes iso-propyl.

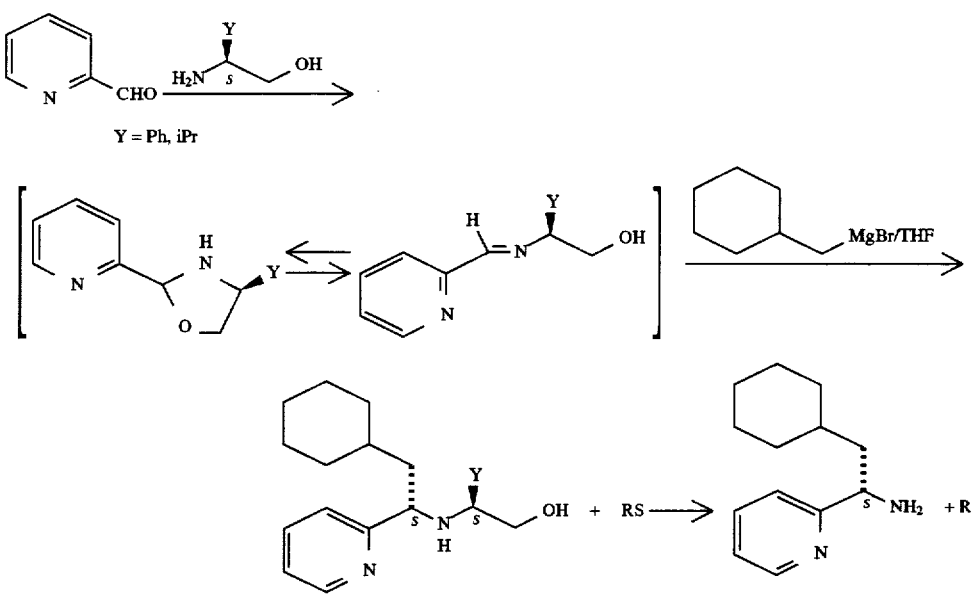

An alternative method of synthesis starts with a cyclohexylmethyl-2-pyridylketone which is reacted, in a condensation reaction, with a valinol to obtain the correspondingly substituted 1,3-oxazolidine derivative which is again in equilibrium with its corresponding imine (cf. the following formula drawing). Catalytic hydrogenation of the imine functionality leads to the corresponding diastereomeric amines. Starting from an R-aminoalcohol, a ratio of the two diastereomers SR:RR of 98:2 is obtained, where the substituent Y denotes a phenyl group. The subsequent oxidative cleaving with sodium periodate leads to the desired amines in the final step of the reaction [C. K. Miao, R. Sorcek and P. J. Jones, Tetrahedron Lett. 34 (14), 2259].

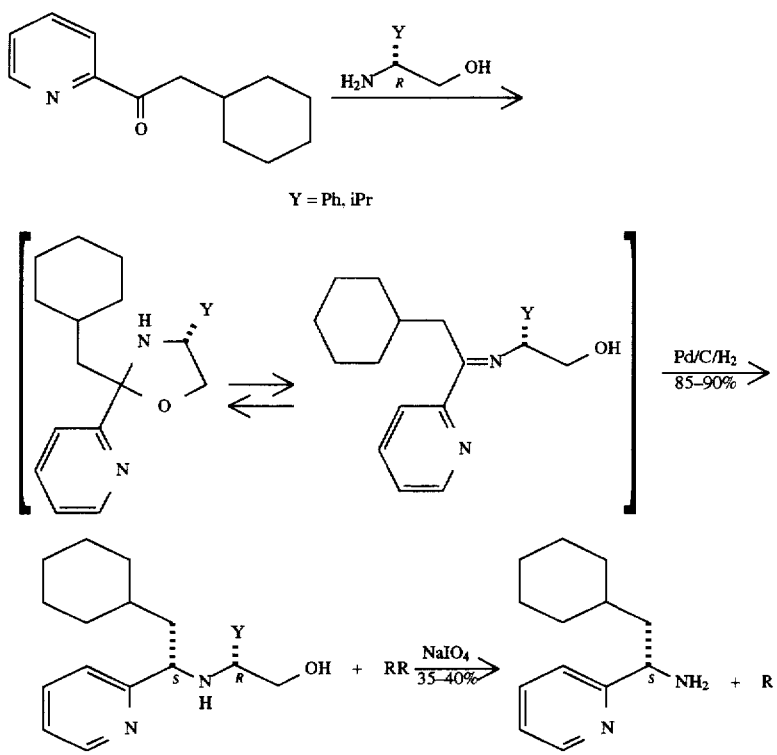

Y = Ph, iPr

In addition, another method is known from the prior art in which a racemic mixture of -(cyclohexylmethyl)-2-pyridylmethylamine is separated via the corresponding diastereomeric amides (by reacting with suitable amino acids) [C. K. Miao, R. Sorcek and J. H. Nagel, Org. Prep. Proced. Int. 24(1), 1987].

The disadvantage of all the methods known from the prior art is, in particular, that the enantiomeric amines obtained in the various reaction sequences have to be separated into the individual enantiomers by time consuming and expensive methods, e.g. by repeated crystallisation of the racemate.

The objective of the present invention is therefore to overcome the disadvantages of the processes known from the prior art.

According to the invention, this objective is achieved by reacting cyanopyridine (2) with a cycloalkylhalomethane of general formula 3 in a Grignard reaction as the first reaction step.

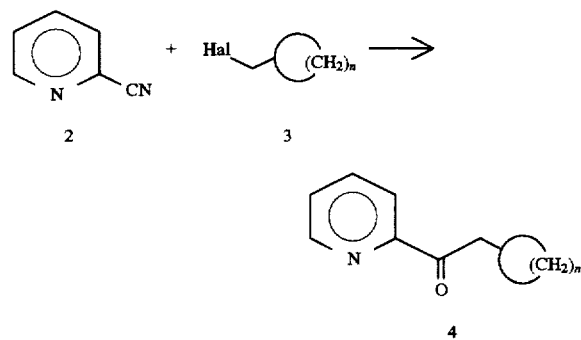

Reactions of this kind are known per se from the prior art [J. March, Advanced Organic Chemistry, 3rd Edition, John Wiley & Sons, New York 1985, p. 828 and cited literature]. The halogen compounds used therein are preferably the corresponding bromocycloalkanes. The addition of the Grignard reagent is appropriately carried out in inert reaction media, including hydrocarbons, such as, for example, petroleum ether fractions or alkylaromatic compounds, such as toluene, or dialkylethers, such as diethylether. It is most preferable to use methyl-tert.-butylether as the reaction medium. It is also possible to use mixtures of the above solvents.

The reaction temperature can be freely selected, within wide limits, and is restricted only by insufficient rate of reaction at excessively low temperatures, and by the formation of by-products or decomposition products and by the physical properties of the reaction medium at excessively high temperatures. A reaction temperature in the range from 40° to 70° C. is preferred, the temperature range from 50° to 60° C. being particularly preferred. The Grignard reaction is preferably carried out in the presence of trialkylhalosilanes, of which trimethylchlorosilane is particularly preferred.

The ketimines initially prepared in this way are hydrolysed with the aid of acids, preferably dilute inorganic acids and most preferably semi-concentrated hydrochloric or sulphuric acid.

The ketone of general formula 4 resulting from the hydrolysis reaction is reacted in the next step with enantiomerically pure phenylethylamines of formula 5 under the reaction conditions of azeotropic dehydration, i.e. under reflux conditions with solvents capable of azeotrope formation with water, such as halogenated hydrocarbons such as chloroform, or hydrocarbons such as benzene or toluene, of which toluene is particularly preferred, to obtain the corresponding ketimines of general formula 6. The entraining agent used is preferably a halogenated hydrocarbon, such as, for example, dichloromethane or chloroform, or an aromatic or alkylaromatic compound; toluene is particularly preferred.

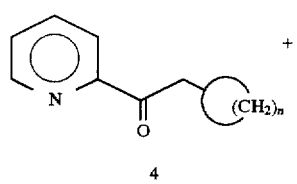

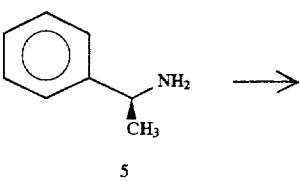

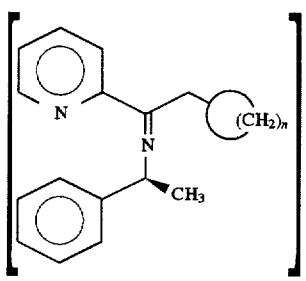

The adjuvants which catalyse this dehydration are well known from the prior art. Preferably, sulphonic acid derivatives are used, of which the hydrate of p-toluenesulphonic acid is particularly preferred.

It is particularly preferable to carry out the dehydration reaction in the presence of silica gel.

After dehydration has been carried out the reaction mixture is suction filtered and concentrated by evaporation in vacuo, preferably in a water jet vacuum.

In order to reduce the ketimines of general formula 6 thus obtained, they are first dissolved in a polar solvent which is inert under reductive reaction conditions. Lower alkanols are preferred, of which ethanol is particularly preferred.

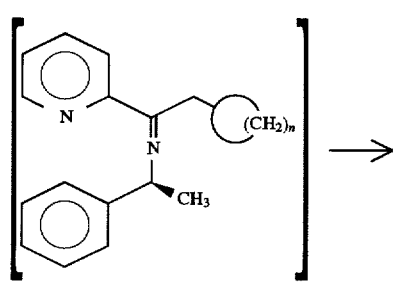

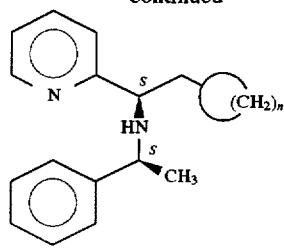

S,S-Diastereomer

7a

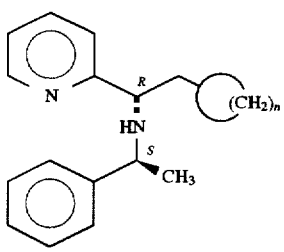

R,S-Diastereomer

7b

The reduction of ketimines is known per se from the prior art and is carried out using complex hydrides. Complex hydrides of boron or aluminium are preferred. It is particularly preferable to use sodium borohydride or lithium aluminium hydride as the reducing agent [N. G. Gaylord. Reduction with Complex Metal Hydrides. Wiley, New York 1965; A. Hajos. Complex Hydrides, Elsevier, New York 1979; V. Bazant, M. apka, M. erny, V. Chvalovsky, K. Kochloefl, M. Kraus and J. Malek, Tetrahedron Lett. 9, 3303].

Appropriately, the temperature should not exceed 10° C. when the solution of reducing agent is added, e.g. when using sodium borohydride. After it has been added, the reaction solution is heated to ambient temperature, i.e. about 25° C. and then adjusted to a pH greater than 8, preferably 9, using a basic compound, preferably an aqueous solution of an alkali metal hydroxide, most preferably with (1N) aqueous sodium hydroxide solution. After the solvent has been distilled off the residue is extracted with a non-polar solvent, preferably with a dialkylether, most preferably methyl-tert.-butylether, against water.

The mixture of the diastereomeric amines of general formulae 7a and 7b thus obtained is reacted with suitable acids, such as, preferably, fumaric or oxalic acid, fumaric being particularly preferred, so as to achieve a concentration of the desired amine.

In order to prepare the diastereomeric salts the amines 7a and 7b are first dissolved in an inert solvent. The preferred solvents are lower alkylesters ($C_{1-6}$) of lower carboxylic acids ($C_{1-6}$), of which ethyl acetate is particularly preferred. To the slightly warmed solution is added, at a temperature in the range from preferably 40° to 60° C. and most preferably 50° C., a solution of a dibasic acid (HXXH) suitable for salt formation with the amine 7a or 7b, in a polar solvent, the solvent used preferably being a lower alkanol, most preferably ethanol.

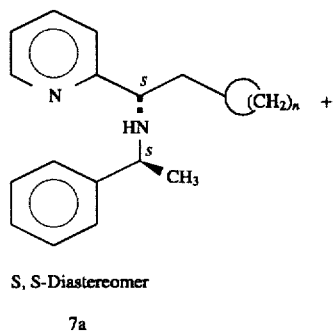

S, S-Diastereomer

7a

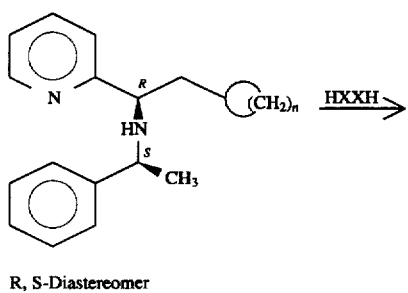

R, S-Diastereomer

7b

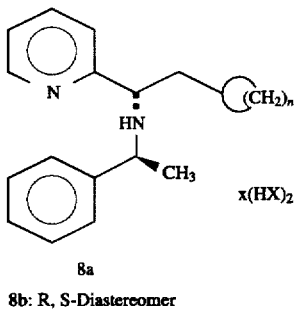

8a

8b: R, S-Diastereomer

The salt 8 of the desired diastereomer thus prepared is isolated and dissolved in a polar solvent, preferably a lower alkanol, most preferably ethanol, at a temperature in the range from 50° to 100° C., preferably in the range from 50° to 65° C., most preferably from 55° to 60° C., and reacted with a hydrogen donor in the presence of a catalyst capable of catalysing hydrogen transfer.

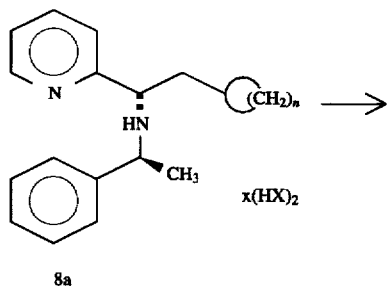

8a

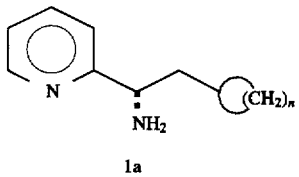

1a

These catalysts and suitable hydrogen donors are also known from the prior art (cf. for example G. Brieger and T. J. Nestrick, Chem.Rev., 74 (1974) 567]. The preferred catalyst is palladium on charcoal, whilst such a catalyst containing 10% palladium is particularly preferred.

Cyclohexene is preferably used as hydrogen donor.

After debenzylation has ended the reaction mixture is cooled to a temperature of about 50° C. and the catalyst is removed and washed with water. The solution of the enantiomeric amine thus obtained is evaporated down in vacuo and then extracted with an extraction agent which is water-immiscible. Preferably, dialkylethers are used as the extraction agents of which methyl-tert.-butylether is particularly preferred.

After washing with water the amine of type 1 (in the present Example 1a) has gone into the aqueous phase, for example in the form of its succinate. The aqueous phase is made alkaline with a basic compound—preferably with ammonia solution and most preferably with concentrated ammonia solution—and extracted with a water-immiscible solvent, preferably a halogenated hydrocarbon, most preferably dichloromethane. After the extracts have been dried and the combined extracts have been evaporated down in vacuo, the desired amine is obtained as a crude product which, after dissolving in a polar solvent, preferably a ketone and most preferably acetone, may be converted, for example, with oxalic acid into the corresponding crystalline oxalate.

The objectives stated above are achieved by means of the steps described in the following Examples. There are other embodiments of the process which will be apparent to anyone skilled in the art reading the present specification. However, it is expressly pointed out that the Examples and the specification associated with them are provided solely for the purposes of explanation and description and should not be regarded as restricting the invention.

Using the method described, for example, 1-S-(2-pyridyl)-2-cyclohexylethylamine may be isolated in a proportion of 96.1% in the form of its semi-oxalate; however, the method according to the invention may also be used successfully to synthesise other desired enantiomers or diastereomers.

EXAMPLE 1

(2-Pyridyl)-cyclohexylmethylketone

To a Grignard solution prepared by refluxing 73 g (3 g-atom) of magnesium and 532 g (3.0 Mol) of bromomethylcyclohexane in 1540 ml of methyl-tert.-butylether for 18 to 20 hours, with the addition of 44 g (0.2 Mol) of trimethylsilylchloride by gentle refluxing at 52°–58° C., are added 208 g (2 Mol) of 2-cyanopyridine—dissolved in 1200 ml of methyl-tert.-butylether—at a temperature in the range from 0°–20° C. and the mixture is reacted for a further hour. Any thick suspension obtained is diluted with a further 800 ml of methyl-tert.-butylether. After the reaction has ended the mixture is decomposed with 1500 ml of water at 5° C. and then treated with 450 ml of semi-concentrated hydrochloric acid at 15°–25° C., with cooling, for a period of about 30 minutes. After 1 hour, the phases are separated. The organic phase is washed with water, dried and concentrated by evaporation using a rotary evaporator at 40° C., under a pressure of about 500 mbar.

The pyridylcyclohexylmethylketone is obtained as a crude oil in a crude yield of 108–109%, with a GC content of 80–89%, corresponding to a yield of 87–96% of theory.
Thin layer chromatography
Ready-made silica gel plate Merck Si 60 F 254
Eluant: cyclohexane/ethyl acetate=80/20 (V/V)
Reagent: UV light 254 nm
Dragendroff-reagent

EXAMPLE 2

1-S-1-(1'-(S)-phenylethan-1-yl)amino-1-(pyridin-2-yl)-2-cyclohexylamine 207 g of pyridyl-cyclohexylmethylketone (GC=89.2%; corresponding to 0.91 Mol) are refluxed with 136 g (1.12 Mol) of S-(-)-1-phenylethylamine, 500 mg of p-toluenesulphonic acid hydrate and 136 g of Merck silica gel (0.063–0.2 mm) in 2100 ml of toluene for 4 to 5 hours using a water separator.

Then the reaction mixture is suction filtered and evaporated down using a rotary evaporator. The residue is combined with 2100 ml of ethanol and 38.6 (1.02 Mol) of NaBH₄ in solid form are added to the solution in the course of 40 minutes, whilst the temperature is maintained at about 10° C. The mixture is allowed to react for a further 3.5 hours, during which time the internal temperature rises to +25° C. It is adjusted to pH 9 using 60 ml of 1N sodium hydroxide solution and the ethanol is distilled off at 40° C. under 80 mbar. The residue is extracted with methyl-tert.-butylether (800 ml+400 ml) and water (1800 ml), the organic phase is dried with sodium sulphate, suction filtered and evaporated down. 285 g of crude oil are isolated with an enantiomer content of SS:RS=90:10%.
Thin layer chromatography
Ready-made silica gel plates Merck Si 60 F 254
Eluant: cyclohexane/ethyl acetate/methanol=80/20/3 (V/V/V)

The mixture of diastereomers is dissolved as a crude oil (about 285 g) in 3990 ml of ethyl acetate at ambient temperature with stirring and combined with a warm solution (50° C.) of 107 g of fumaric acid (0.924 Mol) in 1800 ml of ethanol.

The mixture is stirred for a further 2 hours at ambient temperature and suction filtered.

The crystals thus isolated are dried at 60° C. in a vacuum drying cupboard under a pressure of about 120 mbar over a period of about 6 hours until their weight remains constant.

Yield: 201.6 g of S.S-diastereomeric fumaric acid salt (1:1) =52.4% based on the pyridylketone
Melting point: 98°–102° C.
Chiral HPLC: S.S-enantiomer 99.7%

EXAMPLE 3

1-S-(2-Pyridyl)-2-cyclohexylethylamine 40 g (0.094 Mol) of S.S-diastereomeric fumaric salt (1:1) are dissolved in 800 ml of ethanol at an internal temperature of 55° to 60° C. 80 g (0.94 Mol) of cyclohexene are quickly added thereto and a suspension of 12.8 g of palladium/charcoal (10% E 10 ND of Degussa AG) and 120 ml of water is added. The mixture is refluxed for 4–5 hours. The reaction mixture is then cooled to a temperature of 50° C. and suction filtered to remove the catalyst, which is rinsed with 20 ml of demineralised water. The clear solution is evaporated down using a rotary evaporator at 40 C under 120 mbar until an oily residue is obtained. This is extracted with methyl-tert.-butylether (2×100 ml) and washed with water (1×80 ml). The amine is then contained as its succinate in the aqueous phase.

This is made alkaline with 15 ml of concentrated ammonia and extracted with dichloromethane (2×100 ml). After the combined organic extracts have been dried with Na₂SO₄ they are suction filtered and evaporated down using a rotary evaporator at 40° C. under 600 mbar until an oily residue remains. 11.9 g (0.0582 Mol) of the crude product are obtained in the form of an oil. This is dissolved in 150 ml of acetone and combined with a solution of 2.62 g of oxalic acid (0.0291 Mol) in 35 ml of acetone. The neutral oxalate precipitated is suction filtered after 1 hour's stirring, washed with a little cold acetone (20 ml) and dried in a vacuum dryer at 60° C. under a pressure of 100 mbar for a period of 5 hours.

Yield: 11.92 g of 1-S-(2-pyridyl)-2-cyclohexylethylamine× ½oxalate corresponding to 57.1% of theory based on the fumarate used Melting point: 161°–164° C.

Chiral HPLC: Content of 1-S-(2-pyridyl)-2-cyclohexylethylamine 96.1%

Thin layer chromatography
Ready-made silica gel plates Merck Si 60 F 254
Eluant: dichloromethane/methanol/conc. ammonia=90/10/0.5 (V/V/V)
R_f value: about 0.5–0.6

What is claimed is:

1. A process for preparing an enantiomerically pure pyridylcycloalkylethylamine of formula (1a) or (1b):

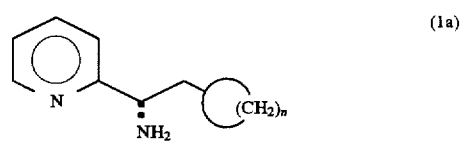

(1a)

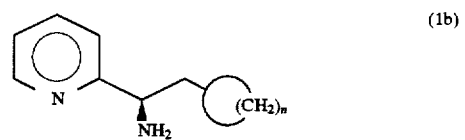

(1b)

wherein n denotes an integer 2, 3, 4, 5, 6 or 7 comprising the following reaction steps:

(a) a cyanopyridine of formula (2) is reacted with a halomethylcycloalkane of formula (3) in the presence of magnesium in an inert reaction medium and after the reaction has ended, the reaction mixture is hydrolyzed under acidic conditions and the resulting ketone of formula (4) is isolated;

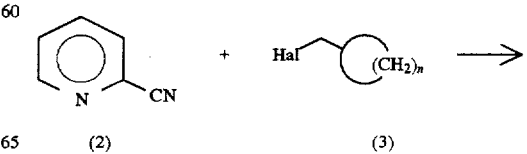

(2)    (3)

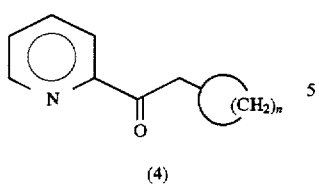

(4)

(b) the ketone of formula (4) is reacted with R- or S-phenylethylamine of formula (5) in a dehydration reaction, optionally in the presence of a substance which catalyzes dehydration, and the resulting ketimine of formula (6) is isolated;

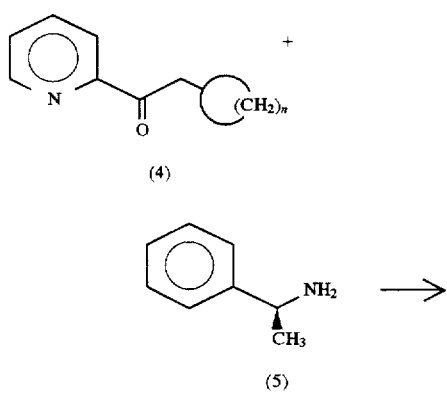

(c) the ketimine of formula (6) is reacted with a reducing agent in an inert polar solvent, and after reduction has ended, the pH is adjusted to a value greater than 8 with an aqueous solution of an alkaline compound and the amine diastereomers of formula (7a) and (7b) resulting from the reduction are extracted and isolated from the reaction mixture using a non-polar solvent;

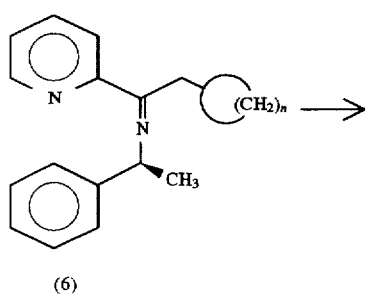

(6)

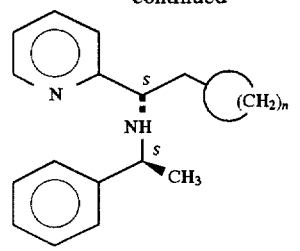

S,S-diastereomer (7a)

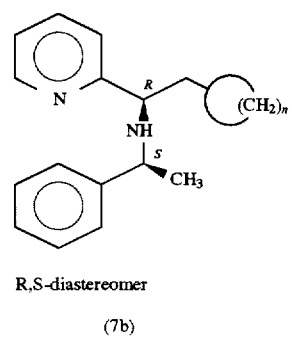

R,S-diastereomer (7b)

(d) the amine diastereomers of formula (7a) and (7b) are reacted with a suitable acid in an inert solvent, the acid capable of salt formation with the amine and being dissolved in a lower alcohol before being added to the solution of diastereomers, and in this way, the amine diastereomers of formula (7a) and (7b) are converted to the corresponding diastereomeric salts, concentration of the desired diastereomeric salt is achieved and the corresponding diastereomer is isolated in the form of its salt of formula (8a) or (8b);

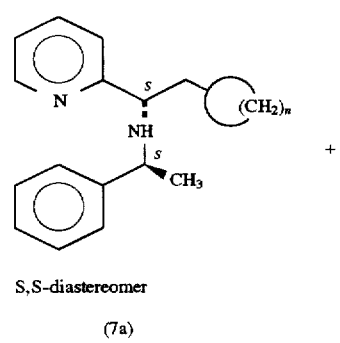

S,S-diastereomer (7a)

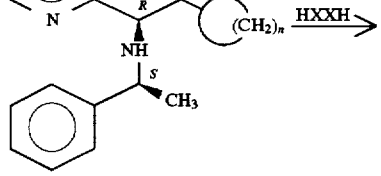

R,S-diastereomer (7b)

-continued

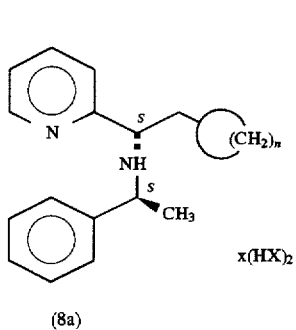

(8a)

(8b): R,S-diastereomer (e) the diastereomeric salt (8a) or (8b) is dissolved or suspended in a polar solvent and reacted at a temperature in the range from 50° to 100° C. with a hydrogen donor in the presence of a catalyst capable of catalyzing hydrogen transfer and the pyridylcycloalkylethylamine of formula (1a) or (1b) produced in this way is released from its salt using a basic compound and isolated; and

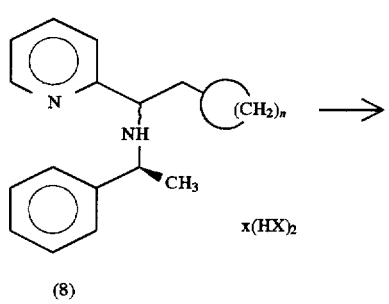

(8)

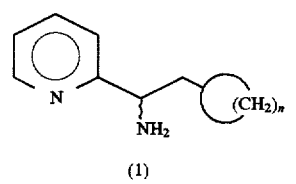

(1)

(f) the pyridylcycloalkylethylamine of formula (1a) or (1b) thus prepared is, if desired, dissolved in a polar solvent and is converted to its corresponding salt using an inorganic or organic acid and isolated.

2. The process as recited in claim 1, characterized in that (a) a cyanopyridine of formula (2) is reacted with a halomelthylcycloalkane of formula (3) in the presence of magnesium in a hydrocarbon or in a dialkylether at a temperature in the range from 40°–70° C., optionally in the presence of a trialkylhalosilane, and after the reaction has ended, the reaction mixture is hydrolyzed using a dilute inorganic acid and the resulting ketone of formula (4) is isolated;

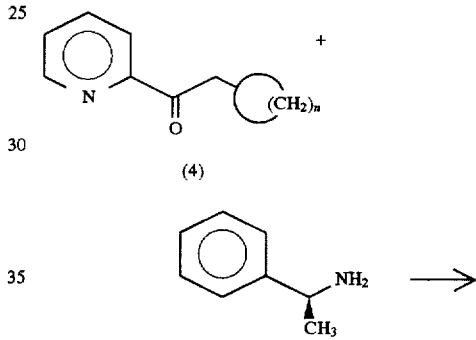

(b) the ketone of formula (4) is reacted with R- or S-phenylethylamine of formula (5) in a dehydration reaction under reflux conditions in a solvent capable of azeotrope formation with water in the presence of a sulphonic acid derivative which catalyzes the condensation reaction or in the presence of silica gel, and the resulting ketimine of formula (6) is isolated;

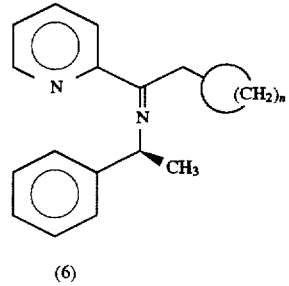

(c) the ketimine of formula (6) is dissolved in an alcohol and reduced with a complex hydride of boron or aluminum at a temperature below 10° C., and after reduction has ended, the pH is adjusted to a value greater than 8 with an aqueous solution of an alkali metal hydroxide and the amine diastereomers of formula (7a) and (7b) resulting from the reduction are extracted and isolated from the reaction mixture using a dialkylether;

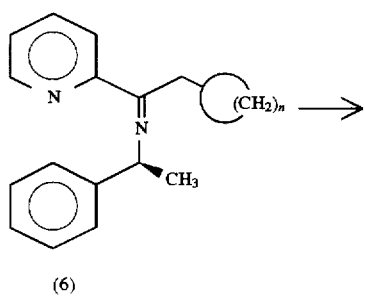

(6)

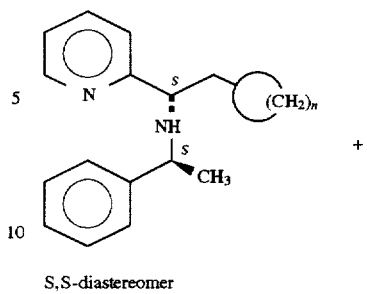

S,S-diastereomer (7a)

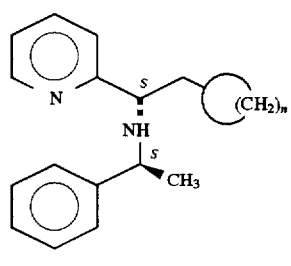

S,S-diastereomer (7a)

+

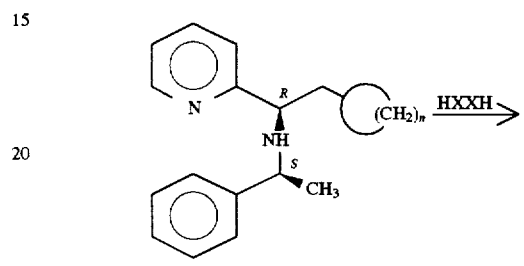

R,S-diastereomer (7b)

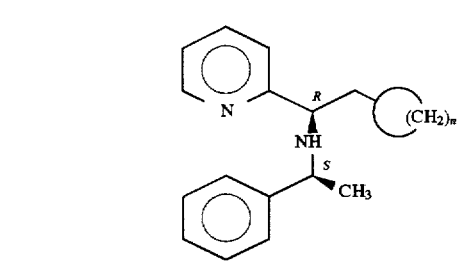

R,S-diastereomer (7b)

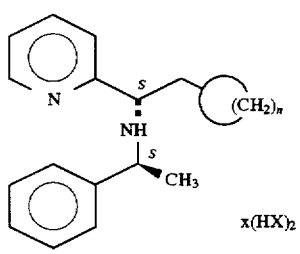

(8a)

(8b): R,S-diastereomer (d) the amine diastereomers of formula (7a) and (7b) are reacted with an organic acid in a lower alkylester of a lower carboxylic acid at a temperature in the range from 40°–600° C., the acid being capable of salt formation with the appropriate amine and being dissolved in a lower alcohol before addition to the solution of the diastereomers, and the amine diastereomers of formula (7a) and (7b) are converted to the corresponding diastereomeric salts, concentration of the desired diastereomeric salt is achieved and the corresponding diastereomer is isolated in the form of its salt of formula (8a) or (8b);

(e) the diastereomeric salt (8a) or (8b) is dissolved or suspended in a lower alkanol at a temperature in the range from 50° to 65° C. and reacted with a hydrogen donor in the presence of a palladium or carbon catalyst capable of catalyzing hydrogen transfer and the pyridylcycloalkylethylamine of formula (1a) or (1b) produced in this way is released from its salt using a nitrogen-containing base and isolated; and

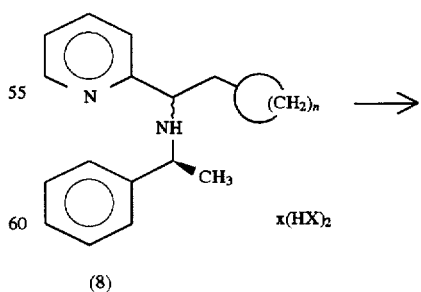

(8)

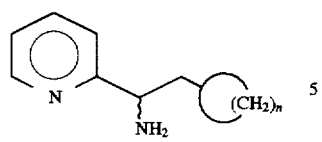

(1)

(f) the pyridylcycloalkylethylamine of formula (1a) or (1b) thus prepared is, if desired, dissolved in a ketone and converted to its corresponding salt using a carboxylic acid and isolated.

3. The process as recited in claim 2, characterized in that (a) a cyanopyridine of formula (2) is reacted with a bromomethylcycloalkane of formula (3) in methyl-tert.-butylether at a temperature in the range from 50°–60° C., in the presence of trimethylchlorosilane, and after the reaction has ended, the reaction mixture is hydrolyzed using semi-concentrated hydrochloric acid or sulphuric acid and the resulting ketone of formula (4) is isolated;

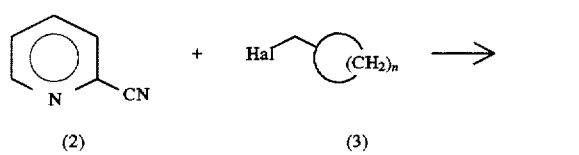

(2)     (3)

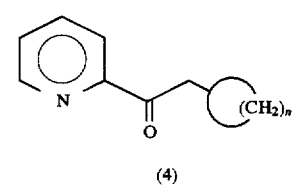

(4)

(b) the ketone of formula (4) is reacted with R- or S-phenylethylamine of formula (5) in a dehydration reaction using azeotropic distillation with toluene and in the presence of silica gel and the resulting ketimine of formula (6) is isolated;

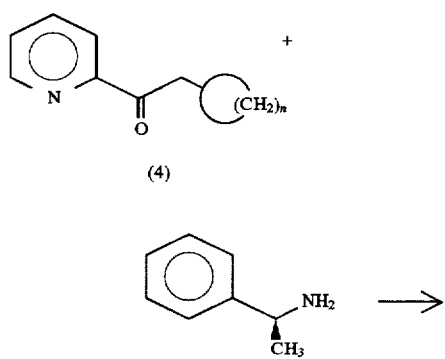

(5)

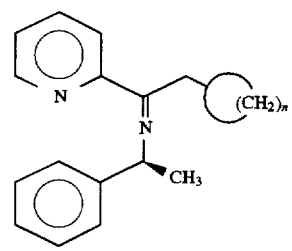

(6)

(c) the ketimine of formula (6) is dissolved in ethanol and reduced with sodium borohydride or lithium aluminum hydride at a temperature below 10° C., and after the reduction has ended, the pH is adjusted to a value greater than 9 with an aqueous sodium hydroxide solution and the amine diastereomers of formula (7a) and (7b) resulting from the reduction are extracted and isolated from the reaction mixture using methyl-tert.-butylether;

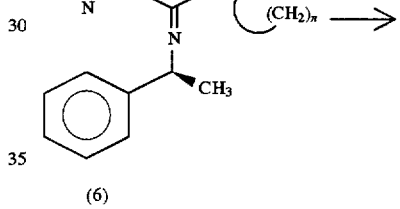

(6)

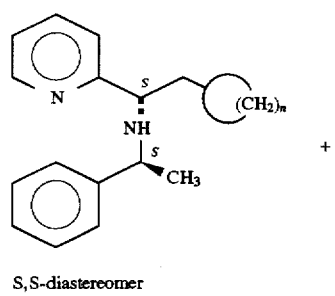

S,S-diastereomer (7a)

+

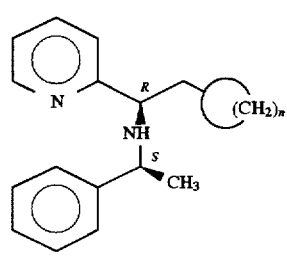

R,S-diastereomer (7b)

(d) the amine diastereomers of formula (7a) and (7b) are reacted with fumaric or oxalic acid in a lower alkylester of a lower carboxylic acid at a temperature of 500° C., the fumaric or oxalic acid being dissolved in ethanol before being added to the solution of the diastereomers, and in this way, the amine diastereomers of formula (7a) and (7b) are converted to the corresponding diastereomeric fumarates or oxalates and the desired diastereomer is concentrated and the corresponding diastereomer is isolated in the form of its salt of formula (8a) or (8b);

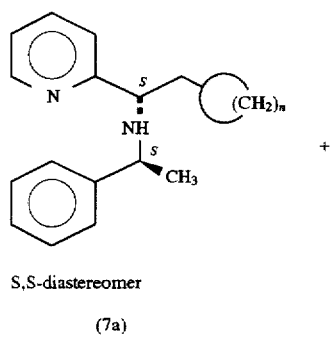

S,S-diastereomer (7a)

+

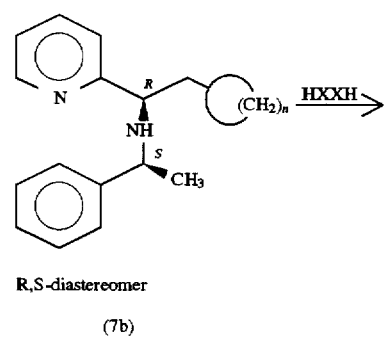

R,S-diastereomer (7b)

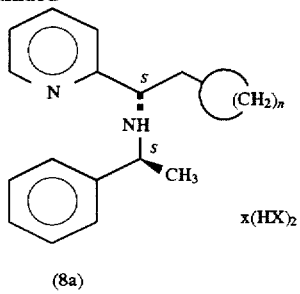

(8a)

(8b): R,S-diastereomer (e) the diastereomeric salt (8a) or (8b) is dissolved or suspended in ethanol at a temperature in the range from 55° to 60° C. and reacted with cyclohexene as the hydrogen donor in the presence of palladium on charcoal (10% Pd) and the pyridylcycloalkylethylamine of formula (1a) or (1b) produced in this way is released from its salt using an ammonia solution; and

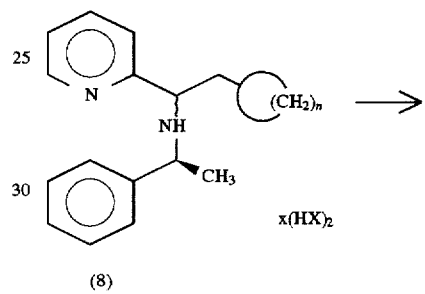

(8)

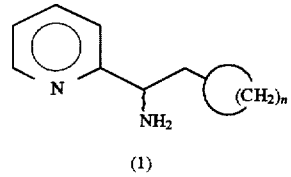

(1)

(f) the pyridylcycloalkylethylamine of formula (1a) or (1b) thus prepared is optionally converted with oxalic acid in acetone to the corresponding oxalate which is then isolated.

* * * * *